United States Patent [19]

Schulz, Jr. et al.

[11] Patent Number: 5,126,470

[45] Date of Patent: Jun. 30, 1992

[54] PREPARATION OF SILOXANES

[75] Inventors: William J. Schulz, Jr.; John L. Speier, both of Midland County, Mich.

[73] Assignee: Dow Corning Corporation, Midland, Mich.

[21] Appl. No.: 683,212

[22] Filed: Apr. 10, 1991

[51] Int. Cl.$^5$ ................................................ C07F 7/08
[52] U.S. Cl. ...................................... 556/453; 556/456
[58] Field of Search ................................. 556/453, 456

[56] References Cited

U.S. PATENT DOCUMENTS

| | | | |
|---|---|---|---|
| 2,629,725 | 2/1953 | Hyde | 556/453 X |
| 3,647,846 | 3/1972 | Hartlein et al. | 556/453 X |
| 4,060,537 | 11/1977 | Maass et al. | 556/453 X |
| 4,395,563 | 7/1983 | Hayes | 556/456 X |
| 4,578,494 | 3/1986 | Marko et al. | 556/452 |

OTHER PUBLICATIONS

Lee, J. G., and Kang, K. K., "Selinium Dioxide Catalyzed Conversion of Alcohols to Alkyl Chlorides by Chlorotrimethylsilane", J. Org. Chem. 1988, 53, pp. 3634–3637.

Primary Examiner—Paul F. Shaver
Attorney, Agent, or Firm—Robert L. McKellar

[57] ABSTRACT

This invention relates to a non-aqueous method for preparing disiloxanes, copolymeric siloxanes, and cyclic siloxanes containing phenyl, higher alkyl, and certain reactive groups bonded to silicon atoms using selenium dioxide as a catalyst. The siloxanes which are formed using this method can be separated from the reaction mixture and purified.

1 Claim, No Drawings

PREPARATION OF SILOXANES

This invention deals with a process to produce siloxanes. More specifically, this invention deals with a method to prepare disiloxanes, copolymeric siloxanes, and cyclic siloxanes containing phenyl, higher alkyl, and certain reactive groups bonded to silicon atoms.

BACKGROUND OF THE INVENTION

It is generally known to prepare polysiloxanes by the aqueous hydrolysis of halosilanes, commonly using acid catalysis. Further, in alternative methods, it is known to prepare polysiloxanes by non-aqueous reactions, for example by reacting chlorosilanes with alcohols. In yet another example of the preparation of polysiloxanes, there is shown in U.S. Pat. No. 4,578,494, issued Mar. 25, 1986 to Marko, et al., that certain metal oxides can be used in conjunction with sulfolanes to "hydrolyze" chlorosilanes to polysiloxanes without the use of water. This patent discloses an extensive review of the literature regarding the use of such metal oxides for that purpose, but does not deal with the metal oxide of the instant invention.

In a most recent article, "Selenium Dioxide Catalyzed Conversion of Alcohols to Alkyl Chlorides by Chlorotrimethylsilane", J. Org. Chem. 1988, 53, 3634–3637, Lee, J. G. and Kang, K. K., describe the use of selenium dioxide as an aid in the preparation of alkyl chlorides using alcohols and certain chlorosilanes. In this article, at page 3636, the authors describe the reaction as being one in which the selenium dioxide is converted in situ to selenium oxychloride which they describe as a mild chlorinating agent for alcohols, the advantage being that selenium dioxide cannot escape out of the reaction mixture. The reaction is described thus:

$$ROH + 2(CH_3)_3SiCl \xrightarrow{SeO_2} RCl + HCl + [(CH_3)_3Si]_2O,$$

wherein there is was also shown at page 3635 the reaction forming the intermediate selenium oxychloride, viz.

$$2(CH_3)_3SiCl + SeO_2 \longrightarrow (CH_3)_3SiO(O)SeCl \longrightarrow$$

$$SeOCl_2 + [(CH_3)_3Si]_2O$$

it being noted that hexamethyldisiloxane is formed in the reaction. The use of trimethylchlorosilane and the formation of the hexamethyldisiloxane would be entirely expected from researchers seeking alkyl halides, since the alkyl halides have boiling points far greater than that of hexamethyldisiloxane and the separation of the alkyl halides is enhanced thereby. Thus, chlorotrimethylsilane was virtually the only chlorosilane used by the authors in order to obtain a siloxane. However, the authors pointed out, at page 3636, column 2, that the reactions they were dealing with did produce oligomers and polymers of dimethylsiloxane as byproducts from the reaction of dimethyldichlorosilane, and they also reacted trichloromethylsilane with the alcohols, without identifying the resulting products, the authors only noting that the ". . . catalyzed chlorination of alcohols by trichloromethylsilane gave a lower yield of alkyl halides. The reason is not clear yet, but there seems to be a competing reaction of the more reactive trichloromethylsilane with alcohols to produce alkoxysilanes." Thus, the authors of this article recognized that they obtained the products that are obtained when siloxanes are not formed such as alkoxychlorosilanes and fully alkoxylated materials but were not aware of the formation of identifiable materials.

They failed to recognize the value of the use of similar reactions to produce commercially viable disiloxanes and cyclic siloxanes, especially those having phenyl, higher alkyl, and certain reactive organic substituents.

The inventors herein, seeking a catalyst that is neither acid or base, so that the siloxanes can be formed without destroying the substituent groups on the siloxanes in the method, have discovered that disiloxanes and cyclic siloxanes having phenyl groups, higher alkyl groups, and certain reactive organic groups can be prepared by the use of selenium dioxide as the catalyst.

THE INVENTION

This invention relates to a non-aqueous method for producing polysiloxanes, more specifically, this invention relates to a method for producing disiloxanes, copolymeric siloxanes, and cyclic siloxanes having phenyl groups, higher alkyl groups, and certain reactive organic groups on the silicon atoms.

More specifically, this invention deals with a method of preparing siloxanes, said siloxanes having a general formula selected from A. $[(CH_3)_x(R)_ySi]_2O$,
B. $[(CH_3)_{x'}(R)_{y'}SiO]_m$, and
C. $(CH_3)_x(R)_ySiO[(CH_3)_{x'}(R)_{y'}SiO]_nSi(R)_y(CH_3)_x$ said method comprising contacting a chlorosilane having the general formula $$(CH_3)_{x''}(R)_{y''}SiCl_{(4-x''-y'')}$$

wherein each R is independently selected from a group consisting essentially of hydrogen, phenyl, alkenyl groups having up to six carbon atoms, haloalkyl groups and higher alkyl groups containing from 2 to 30 carbon atoms, with an alcohol having the general formula R'OH wherein each R' is independently selected from a group comprising alkyl groups of 1 to 12 carbon atoms, in the presence of $SeO_2$ at a time sufficient and a temperature sufficient to produce the siloxanes A., B., or C., or mixtures thereof; wherein in formula A and C, each x has a value of 0, 1, or 2; each y has a value of 1, 2 or 3, and the sum of $(x+y)$ on each silicon atom does not exceed 3 and, wherein in formula B and C, each x' has a value of 0 or 1, each y' has a value of 1 or 2 and the sum of $(x'+y')$ on each silicon does not exceed 2; x'' has a value 0, 1 or 2; y'' has a value of 1, 2 or 3; $(4-x''-y'')$ has a value of 1 or 2, m has a value of 3 to 10, and n has a value of 1 to 25.

Thus, the method allows for the conversion of monochlorosilanes to disiloxanes, the conversion of dichlorosilanes to cyclic siloxanes, and the conversion of mixed chlorosilanes to copolymeric siloxanes using an alcohol, and selenium dioxide as the catalyst. It could not be predicted that selenium dioxide would allow the production of the siloxanes on the basis of what is taught in the prior art.

For purposes of this invention, the chlorosilanes of this invention are those having the general formula $$(CH_3)_{x''}(R)_{y''}SiCl_{(4-x''-y'')}$$

wherein each R is independently selected from a group consisting essentially of hydrogen, phenyl, alkenyl groups having up to six carbon atoms, haloalkyl groups and higer alkyl groups containing from 2 to 30 carbon atoms. Thus, for example, the chlorosilanes are those in which each R is selected from hydrogen, phenyl, alkenyl groups such as $CH_2=CH-$, $CH_2=CHCH_2-$, $CH_2=CHCH_2CH_2CH_2CH_2-$, and the like. Also included within the scope of this invention are haloalkyl groups such as chloro- and fluoro-substituted alkyl groups, such as chloromethyl, chloropropyl, chlorobutyl, and 1,1,1,-trifluoropropyl, and fully substituted haloalkyl groups such as $CF_3CF_2CF_2-$ and the like. Also, for purposes of this invention the silanes can be mixed silanes, that is, they can contain varying types of substituents on silicon to give resulting siloxanes with a wide variety of substituent groups appended to the silicon atoms. Specific examples of the monochlorosilanes useful in this invention where $\phi$ is the phenyl group, include $\phi(CH_3)_2SiCl$, $(\phi)_2CH_3SiCl$, $(CH_3)_2(H)SiCl$, $(CH_3)_2(CH_2=CH)SiCl$, $(CH_3)_2(C_{18}H_{37})SiCl$, $(CH_3)_2(C_6H_{13})SiCl$, $(CH_3)_2(CF_3CH_2CH_2)SiCl$, and the like. In addition, dichlorosilanes useful in this invention include, for example, $(CH_3)\phi SiCl_2$, $(CH_3)CH_2=CHSiCl_2$, $\phi CH_2=CHSiCl_2$, $(CH_3)HSiCl_2$, and dimethyldichlorosilane when used with other silanes, and the like.

Mixtures of halosilanes may be used in this invention to prepare mixed siloxanes, for example, dimethyldichlorosilane and vinylmethyldichlorosilane may be used to give a statistical distribution of materials, including the mixed cyclic siloxane, hexamethyldivinyltetrasiloxane.

The halosilane, or mixture of halosilanes is reacted with the metal oxide in the presence of solvents or the reaction can be carried out without the use of solvents. Solvents useable in this invention include any organic solvents that do not react with the selenium dioxide or the chlorosilanes. Preferred solvents are chlorinated alkanes, such as, for example, carbon tetrachloride.

The other reactant in this process is an alcohol. More specifically, the alcohols useful in this invention are those having the general formula R'OH of 1 to 12 carbons atoms. Most preferred are tertiary alcohols, and especially preferred is t-butyl alcohol. It has also been found that neopentyl alcohol is especially useful in this invention.

The process is carried out by combining the $SeO_2$ and the chlorosilane or chlorosilanes, and solvent if desired, in a reaction vessel, and the alcohol is slowly added to the mixture. Then the mixture is stirred for a period of time, either at room temperature or at an elevated temperature, to effect the reaction.

For purposes of this invention, the selenium dioxide is generally used in the 0.5 to 5 weight percent range, based on the weight of the total reactants. More preferred is a selenium dioxide content of about 1 to 3.5 weight percent, and most preferred is a selenium dioxide content of about 1.8 to 2.5 weight percent. The selenium precipitates out after the reaction as selenium metal and is easily separated from the reaction mixture by filtration.

For purposes of this invention, the reaction can be carried out at a temperature range of from about 0° C. to about 100° C., with the preferred temperature range being about 15° C. to about 35° C.

The amount of time that is required to complete the reaction depends on the temperature and the types of chlorosilanes that are being used. Generally, the time that is required to complete the reaction is about 30 minutes to about 5 hours. Preferred for this invention is a time of about 1.5 to 4 hours not including time of addition of the reactants to the reaction vessel.

Upon completion of the reaction, the siloxanes that have been formed can be separated from the reaction mixture and purified if desired.

Now so that those skilled in the art can better appreciate and understand the invention the following examples are given.

EXAMPLE 1

The following is representative of the experiments described in this invention in the following examples.

Into a 250 ml round-bottomed flask were charged 0.500 mole of the desired halosilane and 0.01 mole of $SeO_2$ (2 mole %). If desired, and as indicated, 50 ml of $CCl_4$ was added as solvent. A magnetic stir bar was added, and the system stirred for 15 minutes to react the $SeO_2$ to form $SeOCl_2$ as much as possible. The flask was equipped with a Claisen adapter, and on one neck of the adapter was placed a reflux condenser that was attached to a mineral oil bubbler at the outlet to monitor gas evolution. The other neck of the adapter was equipped with a pressure-equalizing addition funnel containing an appropriate amount of the desired alcohol (0.250 mole when a monochlorosilane is used, and 0.500 mole when a dichlorosilane is used). The alcohol was then added dropwise over the desired period of time, and the system was allowed to stir for an additional period of time or heated to reflux if desired. Products were analyzed by $GC^2$/MSD (capillary glc with mass selective detector) as well as other gas chromatographic methods. The mass of the reaction mixture was measured before and after reaction to determine weight loss and to calculate mass balance. The examples and the results can be found in the following table.

TABLE

| CHLORO SILANE | ALCOHOL | TEMP/TIME | SOLV. | PRODUCTS |
|---|---|---|---|---|
| $MeHSiCl_2$ | t-butyl | ambient add reflux 2 hr | $CCl_4$ | Cyclics: 37.9% MeH pentamer 24.4% MeH tetramer 14.3% MeH trimer 14.8% mixed t-butoxysilanes |
| $Me_2HSiCl$ | t-butyl 2 equiv. | ambient add reflux 2 hr | $CCl_4$ | >90% $(Me_2SiH)_2O$ |
| $\phi HSiCl_2$ | t-butyl | ambient ad reflux 2 hr | $CCl_4$ | Cylics: 17% $\phi H$ tetramer |
| 5-hexenyl $MeSiCl_2$ | t-butyl | ambient ad reflux 16 hr | $CCl_4$ | Cyclics: 17% 5-hexenylMe trimer |

TABLE-continued

| CHLORO SILANE | ALCOHOL | TEMP/TIME | SOLV. | PRODUCTS |
|---|---|---|---|---|
| | | | | 16% 5-hexenylMe trimer (isomeric form) |
| | | | | 6.4% 5-hexenylMe tetramer |

All yields are based on area % by GC$^2$/MSD.
"Me" means "methyl"
"φ" means "phenyl"

What is claimed is:

1. A method of preparing siloxanes, said siloxanes having a general formula selected from
  A. $[(CH_3)_x(R)_ySi]_2O$,
  B. $[(CH_3)_{x'}(R)_{y'}SiO]_m$, and
  C. $(CH_3)_x(R)_ySiO[(CH_3)_{x'}(R)_{y'}SiO]_nSi(R)_y(CH_3)_x$ said method comprising contacting a chlorosilane having the general formula $$(CH_3)_{x''}(R)_{y''}SiCl_{(4-x''-y'')}$$

wherein each R is independently selected from a group consisting essentially of hydrogen, phenyl, alkenyl groups having up to six carbon atoms, haloalkyl groups and higher alkyl groups containing from 2 to 30 carbon atoms, with an alcohol having the general formula R'OH wherein each R' is independently selected from a group comprising alkyl groups of 1 to 12 carbon atoms, in the presence of $SeO_2$ at a time sufficient and a temperature sufficient to produce the siloxanes A., B., C., or mixtures thereof; wherein in formula A and C, each x has a value of 0, 1, or 2; each y has a value of 1, 2 or 3, and the sum of (x+y) on each silicon atom does not exceed 3 and, wherein in formula B and C, each x' has a value of 0 or 1, each y' has a value of 1 or 2 and the sum of (x'+y') on each silicon does not exceed 2; x'' has a value 0, 1 or 2; y'' has a value of 1, 2 or 3; (4−x''−y'') has a value of 1 or 2, m has a value of 3 to 10, and n has a value of 1 to 25.

* * * * *